(12) United States Patent
Forman et al.

(10) Patent No.: US 7,544,838 B2
(45) Date of Patent: Jun. 9, 2009

(54) LIGANDS FOR ESTROGEN RELATED RECEPTORS AND METHODS FOR SYNTHESIS OF SAID LIGANDS

(75) Inventors: Barry Forman, Irvine, CA (US); Donna Yu, Arcadia, CA (US)

(73) Assignee: City of Hope, Duarte, CA (US)

( * ) Notice: Subject to any disclaimer, the term of this patent is extended or adjusted under 35 U.S.C. 154(b) by 447 days.

(21) Appl. No.: 11/336,515

(22) Filed: Jan. 20, 2006

(65) Prior Publication Data

US 2006/0189825 A1 Aug. 24, 2006

Related U.S. Application Data

(60) Provisional application No. 60/646,128, filed on Jan. 21, 2005.

(51) Int. Cl.
*C07C 243/18* (2006.01)
(52) U.S. Cl. .................. 564/148; 564/150; 514/615
(58) Field of Classification Search ............. 564/148, 564/150; 514/615
See application file for complete search history.

(56) References Cited

U.S. PATENT DOCUMENTS

| | | | | | |
|---|---|---|---|---|---|
| 4,981,784 | A | * | 1/1991 | Evans et al. ................ | 435/6 |
| 5,229,038 | A | * | 7/1993 | Uchino et al. .............. | 252/582 |
| 2005/0266457 | A1 | * | 12/2005 | Palli et al. .................. | 435/6 |

OTHER PUBLICATIONS

Bahadur, S., Varma, R. S., Saxena, M., *Synthesis of some new Mannich bases of N-(4-Hydroxy-3methoxy-benzylidene)-4-methoxy benzoic acid hydrazide as potential biologically active agents*, J. Indian Chem. Soc. 1980, LVII, 918-919.
Barger, P.M. and Kelly D.P., *Fatty Acid Utilization in the Hypertrophied and Failing Heart: Molecular Regulatory Mechanisms*, American Journal of the Medical Sciences, 1999, 318:36.
Carrier, J. C., Deblois, G., Champigny, C., Levy, E., Gigurere, V., *Estrogen related receptor a (ERR a) is a transcriptional regulator of apolipoprotein A-IV and controls lipid handling in the intestine*, J Biol Chem 2004, 52052-52058.
Coward, P., Lee, D., Hull, M. V., Lehmann, J. M., *4-Hydroxytamoxifen binds to and deactivates the estrogen-related receptor gamma*, Proc Natl Acad Sci U S A 2001, 98, 8880-8884.
Giguere, V., *To ERR in the estrogen pathway*, Trends Endocrinol Metab. 2002, 13, 220-225.
Herzog, B., Cardenas, J., Hall, R.K., et al., *Estrogen-related Receptor alpha Is a Repressor of Phosphoenolpyruvate Carboxykinase Gene Transcription*, J. Biological Chemistry, 2006, 281(1):99-106.
Huss, J. M., Kopp, R. P., Kelly, D. P., *Peroxisome proliferator-activated receptor coactivator-1alpha (PGC-1alpha) coactivates the cardiac-enriched nuclear receptors estrogen-related receptor-alpha and —gamma, Identification of novel leucine-rich interaction motif within PGC-1alpha*, J Biol Chem 2002, 277, 40265-40274.
Huss, J. M., Torra, I. P., Staels, B.; Giguere, V., Kelly, D. P., *Estrogen-related receptor {alpha}directs peroxisome proliferator-activated receptor {alpha}signaling in the transcriptional control of energy metabolism in cardiac and skeletal muscle*, Mol Cell Biol 2004, 24, 9079-9091.
Huss, J.M., and Kelly, D.P., *Nuclear Receptor Signaling and Cadiac Energetics*, Circulation Research, 2004, 95:568-578.
Lehman, J.J., and Kelly, D.P., *Gene Regulatory Mechanisms Governing Energy Metabolism during Cardiac Hypertrophic Growth*, Heart Failure Reviews, 2002, 7:175-185.
Luo, J., Sladeck, R., Carrier, J., Bader, J. A., Richard, D. et al., *Reduced fat mass in mice lacking orphan nuclear receptor estrogen-related receptor alpha*, Mol Cell Biol 2003, 23, 7947-7956.
Mootha, V. K., Handschin, C., Arlow, D., Xie, X., St Pierre, J. et al., *Erralpha and Gabpa/b specify PGC-1alpha-dependent oxidative phosphorylation gene expression that is altered in diabetic muscle*, Proc Natl Acad Sci U S A 2004, 101, 6570-6575.
Sack M.N. and Kelly D.P., *The energy substrate switch during development of heart failure: gene regulatory mechanisms*, Int J Mol Med., 1998, Jan;1(1);17-24.
Schreiber, S. N., Emter, R., Hock, M. B., Knutti, D., Cardenas, J. et al., *The estrogen related receptor alpha (ERRalpha) functions in PPARgamma coactivator 1alpha (PGC-1alpha)-induced mitochondrial biogenesis*, Proc Natl Acad Sci U S A 2004, 101, 6472-6477.
Schreiber, S. N., Knutti, D., Brogli, K., Uhlmann, T., Kralli, A., *The transcriptional coactivator PGC-1 regulates the expression and activity of the orphan nuclear receptor estrogen-related receptor alpha (ERRalpha)*, J Biol Chem 2003, 278, 9013-9018.
Skene, W.G., and Lehn., J.P. *Dynamers: Polyacylhydrazone Reversible Covalent Polymers. Component Exchange, and Constitutional Diversity*, 101 PNAS No. 22 at p. 8270-75 (2004).
Sladek, R., Bader, J-A., Giguere, V., *The Orphan Nuclear Receptor Estrogen-Related Receptor alpha Is a Transcriptional Regulator of the Human Medium-Chain Acyl Coenzyme A Dehydrogenase Gene*, Molecular and Cellular Biology, 1997, 17(9): 5400-5409.
Sumi, D., Ignarro, L. J., *Estrogen-related receptor alplha 1 up-regulates endothelial nitric oxide synthase expression*, Proc Natl Acad Sci U S A 2003, 100, 14451-14456.
Tremblay, G. B., Bergeron, D., Giguere, V., *4-Hydroxytamoxifen is an isoform-specific inhibitor of orphan estrogen-receptor-related (ERR) nuclear receptors beta and gamma*, Endocrinology 2001, 142, 4572-4572.
Wang, H., Chen, J., Hollister, K., Sowers, L. C., Forman, B. M., *Endogenous bile acids are ligands for the nuclear receptor FXR/BAR*, Mol Cell 1999, 3, 543-553.
Wende, A. R., Huss, J.M., Schaeffer, P.J., Giguere, V. and Kelly, D.P., *PGC-1alpha Coactivates PDK4 Gene Expression via the Orphan Nuclear Receptor ERRalpha: a Mechanism for Transcriptional Control of Muscle Glucose Metabolism*, Molecular and Cellular Biology, 2005, 25(24):10684-10694.
Willy, P. J., Murray, I. R., Qian, J., Busch, B. B., Stevens, W. C., Jr. et al., *Regulation of PPARgamma coactivator 1alpha (PGC-1alpha) signaling by an estrogen-related receptor alpha (ERRalpha) ligand*, Proc Natl Acad Sci USA, 2004, 101, 8912-8917.

\* cited by examiner

*Primary Examiner*—Shailendra Kumar
(74) *Attorney, Agent, or Firm*—Joseph P. Hamilton; Perkins Coie LLP

(57) ABSTRACT

Estrogen-Related Receptor (ERR) modulating compounds and methods for synthesis of said compounds are described.

4 Claims, 7 Drawing Sheets

XCT790  (Z)-4-hydroxytamoxifen  DY131

Scheme 1

Scheme 2

DY-000,159

C<sub>15</sub>H<sub>14</sub>N<sub>2</sub>O<sub>2</sub>
Mol. Wt.: 254.28

4-Hydroxy-benzoic acid (3-methyl-benzylidene)-hydrazide

Figure 4B

DY162
C₁₄H₁₂N₂O₂
Mol. Wt.: 240.26

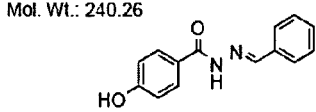

4-Hydroxy-benzoic acid benzylidene-hydrazide

DY163
C₁₅H₁₄N₂O₂
Mol. Wt.: 254.28

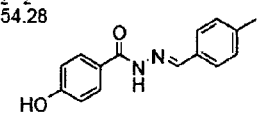

4-Hydroxy-benzoic acid (4-methyl-benzylidene)-hydrazide

DY164
C₁₄H₁₄N₂O₂S
Mol. Wt.: 274.34

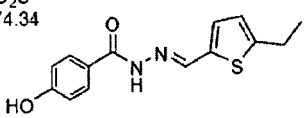

4-Hydroxy-benzoic acid (5-ethyl-thiophen-2-ylmethylene)-hydrazide

DY165
C₁₅H₁₀ClF₃N₂O₂
Mol. Wt.: 342.70

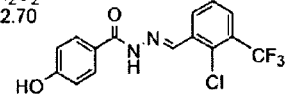

4-Hydroxy-benzoic acid (2-chloro-3-trifluoromethyl-benzylidene)-hydrazide

DY166
C₁₃H₁₂N₂O₂S
Mol. Wt.: 260.31

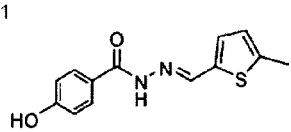

4-Hydroxy-benzoic acid (5-methyl-thiophen-2-ylmethylene)-hydrazide

DY167
C₁₂H₉N₃O₄S
Mol. Wt.: 291.28

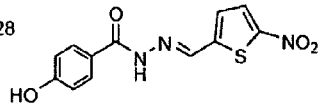

4-Hydroxy-benzoic acid (5-nitro-thiophen-2-ylmethylene)-hydrazide

DY168
C₁₅H₁₁F₃N₂O₂
Mol. Wt.: 308.26

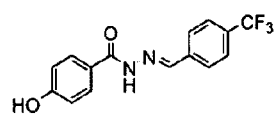

4-Hydroxy-benzoic acid (4-trifluoromethyl-benzylidene)-hydrazide

Figure 4C

DY000,169
C₁₅H₁₄N₂O₃
Mol. Wt.: 270.28

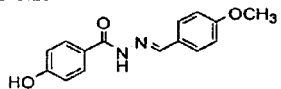

4-Hydroxy-benzoic acid (4-methoxy-benzylidene)-hydrazide

DY000,170
C₁₅H₁₀F₃N₃O₄
Mol. Wt.: 353.25

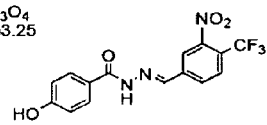

4-Hydroxy-benzoic acid (3-nitro-4-trifluoromethyl-benzylidene)-hydrazide

DY000,171
C₁₄H₁₅N₃O₂
Mol. Wt.: 257.29

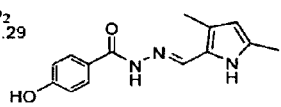

4-Hydroxy-benzoic acid (3,5-dimethyl-1H-pyrrol-2-yl-methylene)-hydrazide

DY000,172
C₁₄H₁₄BrN₃O₂
Mol. Wt.: 336.18

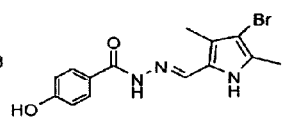

4-Hydroxy-benzoic acid (4-bromo-3,5-dimethyl-1H-pyrrol-2-yl-methylene)-hydrazide DY000,173
C₁₄H₁₄N₂O₃
Mol. Wt.: 258.27

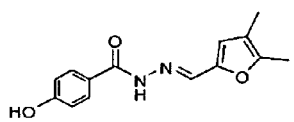

4-Hydroxy-benzoic acid (4,5-dimethyl-furan-2-yl-methylene)-hydrazide

DY000,174
C₁₅H₁₂N₂O₄
Mol. Wt.: 284.27

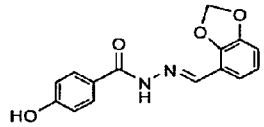

4-Hydroxy-benzoic acid benzo[1,3]dioxo-4-ylmethylene-hydrazide

DY000,175
C₁₄H₁₄N₂O₃
Mol. Wt.: 258.27

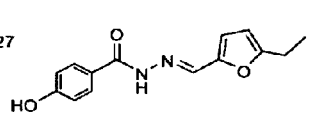

4-Hydroxy-benzoic acid (5-ethyl-furan-2-yl-methylene)-hydrazide

DY000,176
C₁₂H₆ClF₆N₅O
Mol. Wt.: 385.65

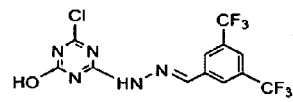

4-[N'-(3,5-Bis-trifluoromethyl-benzylidene)-hydrazino]-6-chloro-[1,3,5]triazin-2-ol

LIGANDS FOR ESTROGEN RELATED RECEPTORS AND METHODS FOR SYNTHESIS OF SAID LIGANDS

CROSS-REFERENCE TO RELATED APPLICATION

The present application claims priority to U.S. Provisional Application No. 60/646,128 (Forman et al.), filed Jan. 21, 2005, the disclosure of which is incorporated by reference herein in its entirety, including drawings.

FIELD OF THE INVENTION

The present invention relates to ligands and methods for synthesis of said ligands.

BACKGROUND OF THE INVENTION

Metabolic disease, including obesity, diabetes and atherosclerosis, is the leading cause of mortality in industrialized nations. It is estimated that over one-third of the United States population is obese and these individuals are at risk for developing diabetes and atherosclerosis. These disorders are responsible for over 500,000 deaths in the United States each year. The growing incidence of this problem has led to intense interest in identifying new molecular targets and new pharmacologic agents to treat and/or prevent these disorders.

Orphan nuclear receptors provide an example of an important class of molecular targets for the treatment of various diseases. Nuclear receptors are ligand-dependent transcription factors that regulate gene expression in response to small-molecule ligands. The orphan receptor ERRα (Estrogen-Related Receptor α) is known to be a regulator of lipid homeostasis. For example, mice lacking ERRα are lean and are resistant to developing obesity when challenged with a high-fat diet. See Luo, J., Sladek, R., Carrier, J., Bader, J. A., Richard, D. et al., *Reduced fat mass in mice lacking orphan nuclear receptor estrogen-related receptor alpha*, Mol Cell Biol 2003, 23, 7947-7956. ERRα is expressed in tissues with a high capacity for β-oxidation of fatty acids including the heart, kidneys, brown adipose tissue and skeletal muscle. See Giguere, V., *To ERR in the estrogen pathway*, Trends Endocrinol Metab. 2002, 13, 220-225. ERRα expression is stimulated by the coactivator PGC-1α; see Schreiber, S. N., Knutti, D., Brogli, K., Uhlmann, T., Kralli, A., *The transcriptional coactivator PGC-1 regulates the expression and activity of the orphan nuclear receptor estrogen-related receptor alpha (ERRalpha)*, J Biol Chem 2003, 278, 9013-9018, and both proteins form a complex that stimulates the expression of genes involved in mitochondrial fatty acid oxidation (medium-chain acylcoenzyme A dehydrogenase, see Huss, J. M., Kopp, R. P., Kelly, D. P., *Peroxisome proliferator-activated receptor coactivator-1alpha (PGC-1alpha) coactivates the cardiac-enriched nuclear receptors estrogen-related receptor-alpha and -gamma, Identification of novel leucine-rich interaction motif within PGC-1alpha*, J Biol Chem 2002, 277, 40265-40274, peroxisome proliferator activated receptor α, see Huss, J. M., Torra, I. P., Staels, B.; Giguere, V., Kelly, D. P., *Estrogen-related receptor {alpha} directs peroxisome proliferator-activated receptor {alpha} signaling in the transcriptional control of energy metabolism in cardiac and skeletal muscle*, Mol Cell Biol 2004, 24, 9079-9091) and oxidative phosphorylation. See Mootha, V. K., Handschin, C., Arlow, D., Xie, X., St Pierre, J. et al., *Erralpha and Gabpa/b specify PGC-1alpha-dependent oxidative phosphorylation gene expression that is altered in diabetic muscle*, Proc Natl Acad Sci USA 2004, 101, 6570-6575; Schreiber, S. N., Emter, R., Hock, M. B., Knutti, D., Cardenas, J. et al., *The estrogen related receptor alpha (ERRalpha) functions in PPARgamma coactivator 1alpha (PGC-1alpha)-induced mitochondrial biogenesis*, Proc Natl Acad Sci USA 2004, 101, 6472-6477. ERRα has also been shown to regulate genes involved in intestinal lipid absorption and satiety signals (apolipoprotein A-IV, see Carrier, J. C., Deblois, G., Champigny, C., Levy, E., Giguere, V., *Estrogen related receptor a (ERR a) is a transcriptional regulator of apolipoprotein A-IV and controls lipid handling in the intestine*, J Biol Chem 2004) and vascular relaxation (endothelial nitricoxide synthase, see Sumi, D., Ignarro, L. J., *Estrogen-related receptor alpha 1 up-regulates endothelial nitric oxide synthase expression*, Proc Natl Acad Sci USA 2003, 100, 14451-14456).

Some forms of heart disease may be related to orphan ERR receptors. Acquired forms of heart failure are associated with switches in the substrate the heart uses for energy. In pressure-induced or volume overload-induced hypertrophy, mitochondrial fatty acid oxidative capacity is reduced and the heart then utilizes glucose as an an energy source (see Huss, J. M., and Kelly, D. P., *Nuclear Receptor Signaling and Cadiac Energetics*, Circulation Research, 2004, 95:568-578). The ERRa/PGC-1a complex is known to activate mitochondrial biogenesis and increase fatty acid oxidation (see Sladek, R., Bader, J-A., Giguere, V., *The Orphan Nuclear Receptor Estrogen-Related Receptor alpha Is a Transcriptional Regulator of the Human Medium-Chain Acyl Coenzyme A Dehydrogenase Gene*, Molecular and Cellular Biology, 1997, 17(9):5400-5409; Schreiber et al., supra; Mootha et al., supra; Willy, P. J., Murray, I. R., Qian, J., Busch, B. B., Stevens, W. C., Jr. et al., *Regulation of PPARgamma coactivator 1alpha (PGC-1alpha) signaling by an estrogen-related receptor alpha (ERRalpha) ligand*, Proc Natl Acad Sci USA, 2004, 101, 8912-8917; Lehman, J. J., and Kelly, D. P., *Gene Regulatory Mechanisms Governing Energy Metabolism during Cardiac Hypertrophic Growth*, Heart Failure Reviews, 2002, 7:175-185; Barger, P. M. and Kelly, D. P., *Fatty Acid Utilization in the Hypertrophied and Failing Heart: Molecular Regulatory Mechanisms*, American Journal of the Medical Sciences, 1999, 318:36; Sack M. N. and Kelly D. P., *The energy substrate switch during development of heart failure: gene regulatory mechanisms*, Int J Mol Med., January 1998; 1(1):17-24). Thus drugs that selectively activate ERRa/PGC-1a should have therapeutic benefits in heart disease by increasing Fatty acid oxidation.

Similarly, ERRa/PGC-1a activates expression of PDK4 thus decreasing glucose oxidation (see Wende, A. R., Huss, J. M., Schaeffer, P. J., Giguere, V. and Kelly, D. P., *PGC-1alpha Coactivates PDK4 Gene Expression via the Orphan Nuclear Receptor ERRalpha: a Mechanism for Transcriptional Control of Muscle Glucose Metabolism*, Molecular and Cellular Biology, 2005, 25(24):10684-10694). Thus drugs that selectively activate ERRa/PGC-1a should have additional therapeutic benefits in heart disease by decreasing glucose utilization.

Additionally, since activation of ERRa/PGC-1a complex is known to increase fatty acid oxidation (see Sladek et al., supra; Schreiber et al., supra; Mootha et al., supra; Willy, et al., supra), drugs that selectively activate ERRa/PGC-1a should be useful for treating obesity and diabetes.

Furthermore, since activation of ERRa/PGC-1a complex is known to decrease PEPCK expression (see Herzog, B., Cardenas, J., Hall, R. K., et al., *Estrogen-related Receptor alpha Is a Repressor of Phosphoenolpyruvate Carboxykinase Gene Transcription*, J. Biological Chemistry, 2006, 281(1): 99-106) and since PEPCK is a rate-limiting step in glucose production in the liver, drugs that selectively activate ERRα/PGC-1a should decrease whole body glucose utilization and be further useful for the treatment of diabetes.

Because of the foregoing, it is desirable to develop compounds, and methods to synthesize said compounds, that can be used to modulate specific receptors in cells and in vivo including estrogen related receptors.

SUMMARY OF THE INVENTION

In one embodiment of the invention, a method for synthesis of 4-hydroxy-benzoic acid (4-diethylamino-benzylidene)-hydrazide is descibed comprising refluxing 4-diethylaminobenzaldehyde with 4-methoxybenzoic acid hydrazide in absolute ethanol wherein said refluxing is conducted in the presence of a catalytic amount of acetic acid.

In another embodiment of the present invention a method for synthesis of 4-hydroxy-benzoic acid (4-diethylamino-benzylidene)-hydrazide is described comprising providing a first solution of 4-methoxy-benzoic acid N'-(4-diethylamino-benzylidene)-N-4-(methyl-benzyl)-hydrazide and a solvent, adding a second solution of boron tribromide and a second solvent, mixing the first and second solutions; and treating the mixed first and second solutions with 1:1 methanol:dichromethane.

In another embodiment of the present invention, a method for synthesis of 4-hydroxy-benzoic acid (4-diethylamino-benzylidene)-hydrazide is described comprising providing a solution of 4-hydroxy-benzoic acid hydrazide, 4-diethylaminoaldehyde and a solvent, adding acetic acid, and refluxing the solution.

In another embodiment of the present invention a compound is descibed wherein said compound is prepared by the process comprising the steps of refluxing 4-diethylaminobenzaldehyde with 4-methoxybenzoic acid hydrazide in absolute ethanol wherein said refluxing is conducted in the presence of a catalytic amount of acetic acid.

In another embodiment of the present invention, a compound is described wheren said compound is prepared by the process comprising the steps of providing a first solution of 4-methoxy-benzoic acid N'-(4-diethylamino-benzylidene)-N-4-(methyl-benzyl)-hydrazide and a solvent, adding a second solution of boron tribromide and a second solvent, mixing the first and second solutions, and treating the mixed first and second solutions with 1:1 methanol:dichromethane.

In another embodiment for the present inventions, a compound is described wherein said compound is prepared by the process comprising the steps of providing a solution of 4-hydroxy-benzoic acid hydrazide, 4-diethylaminoaldehyde and a solvent, adding acetic acid, and refluxing the solution.

DETAILED DESCRIPTION

In order to fully understand the manner in which the above-recited details and other advantages and objects according to the invention are obtained, a more detailed description of the invention will be rendered by reference to specific embodiments thereof.

Figure 1:
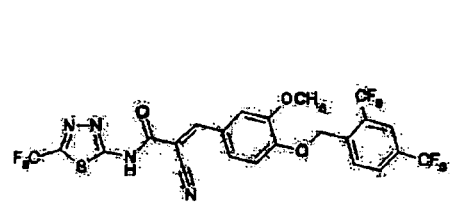
FIG. 1 is shows the chemical structures of several ERR ligands.
Figure 1:
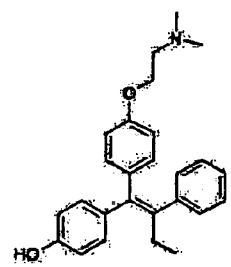
Figure 1:
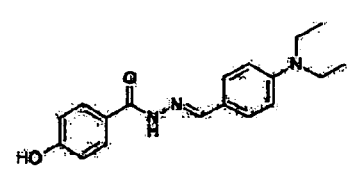

An important advance in the elucidation of orphan receptor biology is the identification of synthetic ligands that can be used to modulate specific receptors in cells and in vivo. For example, FIG. 1 shows a synthetic ERRα antagonist known as XCT790. See Willy, P. J., Murray, I. R., Qian, J., Busch, B. B., Stevens, W. C., Jr. et al., *Regulation of PPARgamma coactivator 1alpha (PGC-1alpha) signaling by an estrogen-related receptor alpha (ERRalpha) ligand*, Proc Natl Acad Sci USA 2004, 101, 8912-8917. This chemical reagent facilitated the discovery of ERRα as a regulator of oxidative phosphorylation, see Mootha et al., and of monoamine oxidase B expression. See Willy et al. XCT790 has no activity on ERRγ, its activity on the related receptors ERRβ, ERα and ERβ have not been reported.

Referring to FIG. 1, chemical structures of several ERR ligands are shown. XCT790 is an ERRα antagonist. (Z)-4-hydroxytamoxifen is a high affinity antagonist for ERα/β, and a low affinity antagonist for ERRβ/γ. DY131 (4-hydroxy-benzoic acid (4-diethylamino-benzylidene)-hydrazide) can an ERRα/β/γ agonist.

Figure 5:
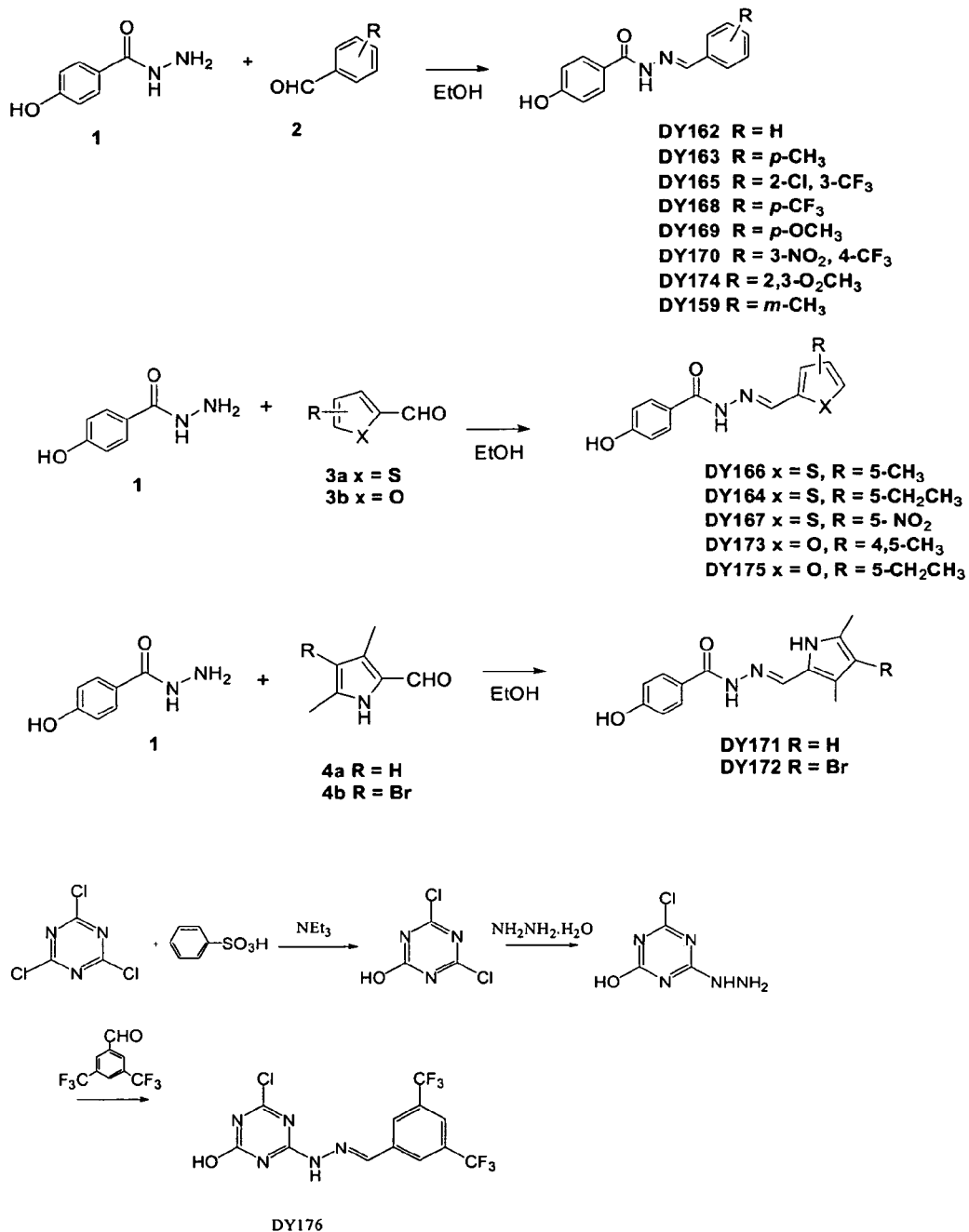
FIG. 5 shows synthesis schemes for several ERR agonists.

Although there has been progress in understanding the physiologic activity of ERRα, little is known about the biological activity of ERRβ and ERRγ. A major factor that is limiting progress in this field is the lack of selective ERRβ/γligands that can be utilized in cell culture and in vivo studies. For example, while (Z)-4-hydroxytamoxifen has been reported to be an antagonist of both ERRβ and ERRγ, see Coward, P., Lee, D., Hull, M. V., Lehmann, J. M., 4-*Hydroxytamoxifen binds to and deactivates the estrogen-related receptor gamma*, Proc Natl Acad Sci USA 2001, 98, 8880-8884; Tremblay, G. B., Bergeron, D., Giguere, V., 4-*Hydroxytamoxifen is an isoform-specific inhibitor of orphan estrogen-receptor-related (ERR) nuclear receptors beta and gamma*, Endocrinology 2001, 142, 4572-4575, this compound is not useful experimentally because it is several orders of magnitude more potent as an ERα and ERβ antagonist. Moreover, no agonist or activating ligands have been reported for any of the ERRs; only antagonists have been identified. We therefore sought to develop an efficient method of synthesis for compounds that could selectively activate ERRα/β/γ with little activity on ERα/β. A series of acyl hydrazone derivatives may activate ERRγ (Keystone Symposia: Orphan Nuclear Receptors, Keystone, Colo., Mar. 2, 2004). Routes for the synthesis of an acylphenylhydrazone derivatives including DY131, 159, 162, 163, 164, 165, 166, 167, 168, 169, 170, 171, 172, 173, 174 and 175 (as shown FIGS. 1 and 5) are shown herein. (See also Skene, W. G., and Lehn., J. P., *Dynamers: Polyacylhydrazone Reversible Covalent Polymers. Component Exchange, and Constitutional Diversity*, 101 PNAS no. 22 at p. 8270-75 (2004).) Moreover, the compounds were evaluated for their potential to act as selective ERRα/β/γ agonists.

Figure 2:
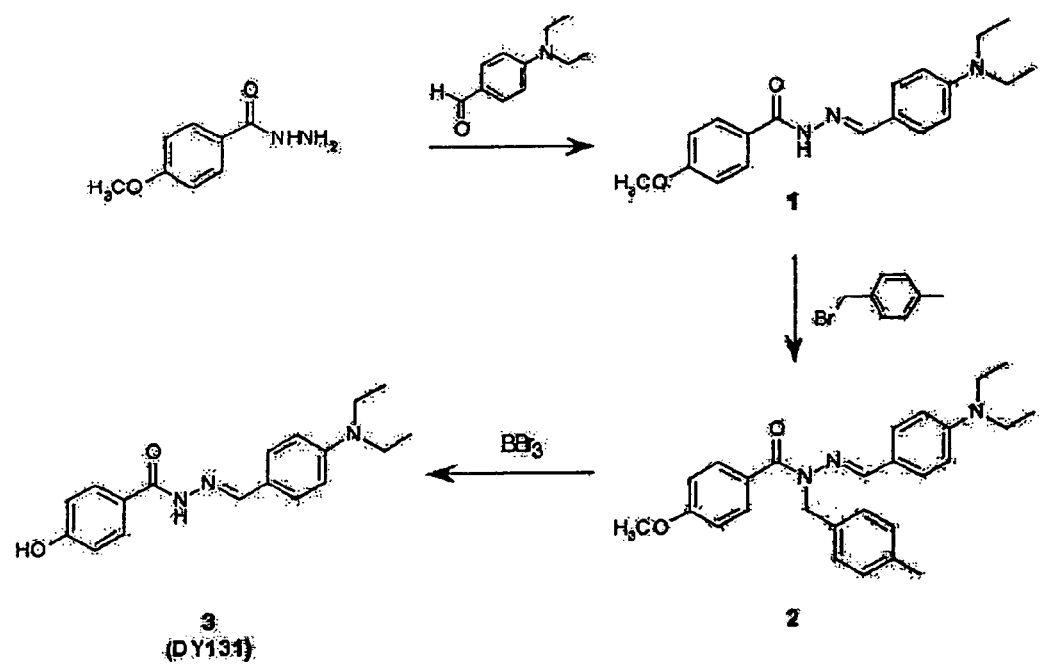
FIG. 2 shows a scheme for the synthesis of DY131.

Referring to FIG. 2, in one embodiment of the invention the synthesis of DY131 may be performed by a direct condensation of 4-hydroxybenzoic acid hydrazide with 4-diethylaminobenzaldehyde. However, because of the uncertainty in using an unprotected hydroxyl, we initially used 4-methoxybenzoic acid hydrazide. 4-diethylaminobenzaldehyde was condensed with 4-methoxybenzoic acid hydrazide by refluxing in absolute ethanol with a catalytic amount of acetic acid according to the method of Bahadur. See Bahadur, S., Varma, R. S., Saxena, M., *Synthesis of some new Mannich bases of N-(4-Hydroxy-3-methoxy-benzylidene)-4-methoxy benzoic acid hydrazide as potential biologically active agents*, J.

Indian Chem. Soc. 1980, LVII, 918-919. This resulted in a 76% yield of 4-methoxy-benzoic acid (4-diethylamino-benzylidene)-hydrazide (compound 1). We found that direct conversion of compound 1 to DY131 (compound 3, 4-hydroxy-benzoic acid (4-diethylamino-benzylidene)-hydrazide) with boron tribromide gave low yields.

Referring to FIG. 2, thus, a two-step procedure was explored whereby the amine of compound 1 was protected prior to conversion to compound 3. Specifically, the amino group of compound 1 was protected by reacting with α-bromo-p-xylene to give 4-methoxy-benzoic acid N'-(4-diethylamino-benzylidene)-N-(4-methyl-benzyl)-hydrazide (compound 2). This was followed by the simultaneous demethylation and deprotection of the N-benzyl group of compound 2 by ether cleavage with boron tribromide. This produced compound 3, with an overall yield of 27%.

Figure 3:
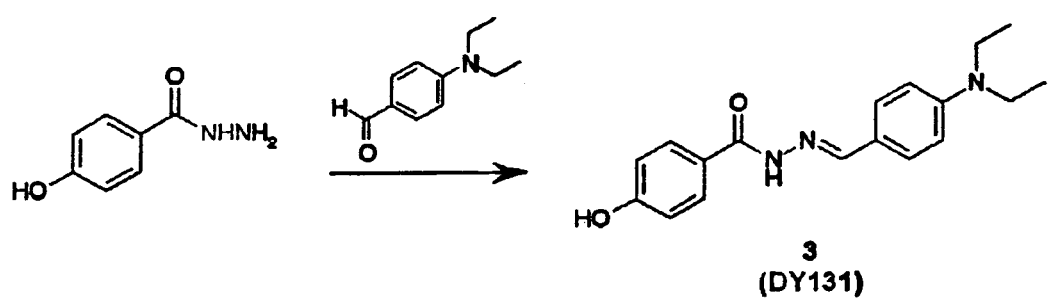
FIG. 3 shows another scheme for the synthesis of DY131.
Figure 4A:
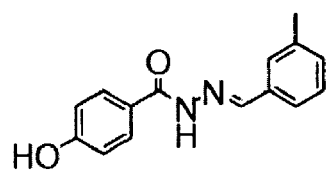
FIG. 4 shows the chemical structures of several ERR agonists.

Referring to FIG. 3, a more efficient procedure for the synthesis of DY131, e.g., one that replaces the three-step procedure of scheme 1 with a single step synthesis, is described. DY131 is synthesized by direct condensation of 4-hydroxybenzoic acid hydrazide with 4-diethylaminobenzaldehyde (scheme 2). The phenolic hydroxyl and the hydrogen of the secondary amine remained unchanged during the reaction and DY131 was successfully synthesized in this one-pot reaction with a yield of 65%.

DY131 was evaluated for selectivity and efficacy in modulating the transcriptional activity of ERRα/β/γ and ERα/β. CV-1 cells were transfected with appropriate reporter constructs and expression vectors (reporter plasmid:Gal-ERR:PGC-1a=0.4:0.035:0.035) and the fold activation of the reporter construct was determined at several concentrations of DY131 as shown in Table 1, which shows cell-based reporter gene assays examining the fold activation of ERR and ER in response to DY131 and β-estradiol. DY131 failed to activate the reporter construct for ERRα at any of the concentrations tested. In contrast, DY131 resulted in 3-4 fold activation of ERRβ at concentrations of 10-30 μM. Activity on ERRγ was even more pronounced with 5-fold activation at 3 μM and maximal 6.6-fold activity observed at 30 μM. Thus, under the conditions used for this assay, DY131 is an ERRβ/γ-specific ligand that displays preferential selectivity for ERRγ at lower concentrations.

Due to the overlap in recognition of (Z)-4-hydroxytamoxifen by both ERR and ER, we also examined the activity of DY131 on ERα and ERβ. DY131 failed to activate or inhibit either of these receptors whereas the control ligand, β-estradiol, resulted in the expected 5-6 fold activation. These data demonstrate that DY131 is a selective agonist of ERRα/β/γ with no activity on the related receptors ERα and ERβ. This selective activity establishes DY131 as a novel pharmacologic tool to study the biological activities of ERRα/β/γ.

TABLE 1

| Receptor | DY131 (Compound 3) | | | B-estradiol |
|---|---|---|---|---|
| | 3 μM | 10 μM | 30 μM | 100 μM |
| — | 0.8 | 0.7 | 0.9 | 1.1 |
| ERRα | 1.5 | 1.7 | 1.6 | 1.1 |
| ERRβ | 1.9 | 3.1 | 3.8 | 1.0 |
| ERRγ | 5.0 | 5.9 | 6.6 | 0.8 |
| — | 1.0 | 1.1 | 1.0 | 1.0 |
| ERRα | 1.1 | 1.0 | 0.9 | 5.2 |
| ERRβ | 1.1 | 1.0 | 1.2 | 6.2 |

DNA Ratio used for experimental procedure of Table 1 was Reporter 0.42: Receptor Expression vector 0.035:PGC-1a 0.035

However, under different assay conditions (reporter plasmid:Gal-ERR:PGC-1a=0.4:0.00875:0.035) than those described for Table 1, DY131 activated the reporter construct for ERRα (Table 2). The difference in results under different conditions likely reflects the fact that ERRa is strongly activated even without addition of a ligand under these conditions that activation is already maximal so that the effect of DY131 is not detectable. But when the amount of PGC-1a is decreased, the effect of a ligand such as DY131 is seen.

TABLE 2

| Reporter | Receptor Expression vector | PGC-1a | Drug conc (μM): | None | DY 131 | | | | | |
|---|---|---|---|---|---|---|---|---|---|---|
| (0.42) | (0.00875) | (0.035) | | 0 | 0.3 | 1 | 3 | 3 | 10 | 30 |
| GAL4-reporter (UASgx4 Tk-luc) | HRHN-GAL | | | 1.00 | 1.03 | 0.94 | 0.74 | 0.74 | 0.77 | 0.79 |
| GAL4-reporter (UASgx4 Tk-luc) | GAL-hERRa | | | 1.00 | 1.10 | 0.96 | 1.55 | 1.57 | 1.44 | 1.87 |
| GAL4-reporter (UASgx4 Tk-luc) | GAL-L-hERRb | | | 1.00 | 0.84 | 1.05 | 1.26 | 1.15 | 2.14 | 2.46 |
| GAL4-reporter (UASgx4 Tk-luc) | GAL-mERRg | | | 1.00 | 0.87 | 0.92 | 1.26 | 1.70 | 1.49 | 1.91 |
| GAL4-reporter (UASgx4 Tk-luc) | HRHN-GAL | PGC-1a | | 1.00 | 1.00 | 0.65 | 0.72 | 1.09 | 0.69 | 0.81 |
| GAL4-reporter (UASgx4 Tk-luc) | GAL-hERRa | PGC-1a | | 1.00 | 1.69 | 2.07 | 2.43 | 2.47 | 3.75 | 3.31 |
| GAL4-reporter (UASgx4 Tk-luc) | GAL-L-hERRb | PGC-1a | | 1.00 | 1.27 | 1.19 | 1.80 | 2.02 | 2.45 | 2.52 |
| GAL4-reporter (UASgx4 Tk-luc) | GAL-mERRg | PGC-1a | | 1.00 | 1.38 | 1.59 | 2.65 | 2.29 | 2.82 | 3.09 |

Additional compounds were tested for their effects on ERR activation (Tables 3-6). DY159, DY162, DY163 and DY164 as well as DY131 can activate all three ERRs (ERRα/β/γ) in the presence of PGC-1a. In particular DY131, 159, 162 and 163 were more potent activators in the presence of PGC-1a than without, ie they activated ERR at lower doses. Therefore, these compounds have two novel features yet to be reported: a) they are selective ERR modulators or coactivator-selective ligands, i.e., they activate ERR better in the presence of PGC- 1a then the other coactivators that are normally present in CV-1 cells; and b) these are the first synthetic compounds reported to ACTIVATE ERRa. Previously reported compounds repress the constitutive activity of ERRa (see Willy et al., supra)

TABLE 3

| Reporter | Receptor Expression vector | PGC-1a | | DY 159 | | | | |
|---|---|---|---|---|---|---|---|---|
| (0.42) | (0.00875) | (0.035) | drug conc (μM): | 1 | 3 | 3 | 10 | 30 |
| GAL4-reporter (UASgx4 Tk-luc) | HRHN-GAL | | | 0.95 | 1.08 | 1.25 | 1.24 | 1.26 |
| GAL4-reporter (UASgx4 Tk-luc) | GAL-hERRa | | | 1.03 | 1.41 | 1.23 | 1.64 | 2.41 |
| GAL4-reporter (UASgx4 Tk-luc) | GAL-L-hERRb | | | 1.29 | 1.25 | 0.98 | 1.33 | 1.36 |
| GAL4-reporter (UASgx4 Tk-luc) | GAL-mERRg | | | 1.39 | 1.28 | 1.22 | 1.36 | 1.01 |
| GAL4-reporter (UASgx4 Tk-luc) | HRHN-GAL | PGC-1a | | 1.31 | 1.05 | 1.03 | 1.39 | 1.11 |
| GAL4-reporter (UASgx4 Tk-luc) | GAL-hERRa | PGC-1a | | 1.18 | 1.69 | 1.55 | 2.02 | 2.61 |
| GAL4-reporter (UASgx4 Tk-luc) | GAL-L-hERRb | PGC-1a | | 1.38 | 1.79 | 1.47 | 1.89 | 2.45 |
| GAL4-reporter (UASgx4 Tk-luc) | GAL-mERRg | PGC-1a | | 1.16 | 1.45 | 1.80 | 2.70 | 2.56 |

TABLE 4

| Reporter | Receptor Expression vector | PGC-1a | | DY 162 | | | | | |
|---|---|---|---|---|---|---|---|---|---|
| (0.42) | (0.00875) | (0.035) | drug conc (μM): | 0.3 | 1 | 3 | 3 | 10 | 30 |
| GAL4-reporter (UASgx4 Tk-luc) | HRHN-GAL | | | 1.14 | 1.07 | 1.02 | 1.12 | 1.26 | 1.25 |
| GAL4-reporter (UASgx4 Tk-luc) | GAL-hERRa | | | 0.77 | 0.86 | 0.89 | 1.51 | 1.82 | 2.03 |
| GAL4-reporter (UASgx4 Tk-luc) | GAL-L-hERRb | | | 1.09 | 1.05 | 0.87 | 0.96 | 1.57 | 1.48 |
| GAL4-reporter (UASgx4 Tk-luc) | GAL-mERRg | | | 1.04 | 0.89 | 0.92 | 1.40 | 1.88 | 1.59 |
| GALA-reporter (UASgx4 Tk-luc) | HRHN-GAL | PGC-1a | | 1.26 | 1.17 | 1.13 | 1.97 | 1.68 | 1.93 |
| GALA-reporter (UASgx4 Tk-luc) | GAL-hERRa | PGC-1a | | 1.26 | 1.22 | 2.11 | 1.93 | 2.18 | 2.36 |
| GAL4-reporter (UASgx4 Tk-luc) | GAL-L-hERRb | PGC-1a | | 0.77 | 0.78 | 1.06 | 1.65 | 1.79 | 2.61 |
| GAL4-reporter (UASgx4 Tk-luc) | GAL-mERRg | PGC-1a | | 0.92 | 1.06 | 1.53 | 1.63 | 2.45 | 2.46 |

TABLE 5

| Reporter | Receptor Expression vector | PGC-1a | | DY 163 | | | | | |
|---|---|---|---|---|---|---|---|---|---|
| (0.42) | (0.00875) | (0.035) | drug conc (μM): | 0.3 | 1 | 3 | 3 | 10 | 30 |
| GAL4-reporter (UASgx4 Tk-luc) | HRHN-GAL | | | 1.01 | 1.10 | 0.93 | 0.78 | 1.01 | 0.83 |
| GAL4-reporter (UASgx4 Tk-luc) | GAL-hERRa | | | 1.37 | 1.25 | 1.26 | 1.41 | 1.20 | 1.67 |
| GAL4-reporter (UASgx4 Tk-luc) | GAL-L-hERRb | | | 1.26 | 1.23 | 1.12 | 1.40 | 1.14 | 1.23 |
| GAL4-reporter (UASgx4 Tk-luc) | GAL-mERRg | | | 1.08 | 1.15 | 0.81 | 1.05 | 1.24 | 0.92 |

TABLE 5-continued

| Reporter | Receptor Expression vector | PGC-1a | | DY 163 | | | | | |
|---|---|---|---|---|---|---|---|---|---|
| (0.42) | (0.00875) | (0.035) | drug conc (µM): | 0.3 | 1 | 3 | 3 | 10 | 30 |
| GAL4-reporter (UASgx4 Tk-luc) | HRHN-GAL | PGC-1a | | 1.01 | 1.16 | 1.05 | 1.24 | 1.13 | 1.01 |
| GAL4-reporter (UASgx4 Tk-luc) | GAL-hERRa | PGC-1a | | 0.78 | 0.89 | 1.43 | 1.91 | 1.90 | 3.23 |
| GAL4-reporter (UASgx4 Tk-luc) | GAL-L-hERRb | PGC-1a | | 1.29 | 1.40 | 1.42 | 1.93 | 2.02 | 2.12 |
| GAL4-reporter (UASgx4 Tk-luc) | GAL-mERRg | PGC-1a | | 1.27 | 1.54 | 1.75 | 1.54 | 2.17 | 2.52 |

TABLE 6

| Reporter (0.42) | Receptor Expression vector (0.00875) | PGC-1a (0.035) | DY 164 |
|---|---|---|---|
| | | drug conc (µM): | 30 |
| GAL4-reporter (UASgx4 Tk-luc) | HRHN-GAL | | 1.46 |
| GAL4-reporter (UASgx4 Tk-luc) | GAL-hERRa | | 1.74 |
| GAL4-reporter (UASgx4 Tk-luc) | GAL-L-hERRb | | 1.89 |
| GAL4-reporter (UASgx4 Tk-luc) | GAL-mERRg | | 2.10 |
| GAL4-reporter (UASgx4 Tk-luc) | HRHN-GAL | PGC-1a | 1.62 |
| GAL4-reporter (UASgx4 Tk-luc) | GAL-hERRa | PGC-1a | 2.75 |
| GAL4-reporter (UASgx4 Tk-luc) | GAL-L-hERRb | PGC-1a | 2.34 |
| GAL4-reporter (UASgx4 Tk-luc) | GAL-mERRg | PGC-1a | 2.45 |

TABLE 7

| | Receptor | | Fold Activation | | | | | |
|---|---|---|---|---|---|---|---|---|
| Reporter | Expression vector | None drug conc (µM): | DY131 30 | DY159 30 | DY162 30 | DY163 30 | DY164 30 | E2 0.1 |
| ERE-TK-luc | hERa | 1.00 | 0.53 | 1.59 | 1.74 | 1.26 | 1.30 | 4.70 |
| ERE-TK-luc | hERb | 1.00 | 1.19 | 1.93 | 1.74 | 1.91 | 1.74 | 6.23 |

Referring to Tables 1-6, cell based transactivation assays were performed in CV-1 cells as described. See Wang, H., Chen, J., Hollister, K., Sowers, L. C., Forman, B. M., *Endogenous bile acids are ligands for the nuclear receptor FXR/BAR*, Mol Cell 1999, 3, 543-553. ERR activity was assayed with a GAL4 reporter construct and fusion proteins containing the ligand binding domains of human ERRα, human ERR β and mouse ERRγ linked to the DNA binding domain of yeast GAL4. Human ERα and ERβ were examined as full-length proteins using an estrogen receptor responsive reporter construct. Fold activation is reported in Table 7.

The compounds DY131, DY159, DY162, DY163 and DY164 are specific for ERRs in that they do not activate the closely related receptors ERa or ERb.

EXAMPLES

General procedures for the following examples are as follows unless otherwise indicated. Organic reagents were purchased from commercial suppliers unless otherwise noted and were used without further purification. All solvents were analytical or reagent grade. All reactions were carried out in flame-dried glassware under argon or nitrogen. Melting points were determined and reported automatically by an optoelectronic sensor in open capillary tubes and were uncorrected. 1H NMR and 13C NMR spectra were measured at 500 MHz and 125 MHz respectively using $CDCl_3$ or $CD_3OD$ as the solvents and tetramethylsilane ($Me_4Si$) as the internal standard. Liquid column chromatography or flash column chromatography under moderate pressure was carried out using columns of an appropriate size packed with silica gel 60 Å (200-400 mesh, Sigma-Aldrich) and eluted as indicated below. All reactions were monitored by TLC on precoated plates (silica gel HLF). TLC spots were visualized either by exposure to iodine vapors or by irradiation with UV light. Organic solvents were removed in vacuum by rotary evaporator. Elemental analyses were performed by Desert Analytics, Tucson, Ariz.

Example I

4-methoxy-benzoic acid hydrazide

A solution of methyl 4-methoxybenzoate, (5.0 g, 0.03 mol) in methanol (20 mL) was treated with hydrazine hydrate (12.0 g, 0.24 mol) and the mixture stirred at 45° C. for 24 hours. The reaction mixture was concentrated and the residue partitioned between EtOAc (50 mL) and water (20 mL). The aqueous layer was extracted with EtOAc (3×20 mL), and the combined organic extracts washed with brine (20 mL), dried over $Na_2SO_4$, and concentrated to give the desired hydrazide (compound 2) as solid which was crystallized by EtOAc giving white solid 4.50 g in 90% yield, mp: 134.3° C. (Aldrich, mp: 136-140° C.). $^1H$ NMR ($CDCl_3$) δ 7.73 (d, 2H), 7.38 (s, 1H), 6.94 (d, 2H), 3.85 (s, 3H), 1.69 (s, 2H). 13C NMR ($CDCl_3$) δ 165.5, 159.6, 125.7, 122.0, 111.1, 52.5. Anal. Calcd for $C_8H_{10}N_2O_2 \cdot \frac{1}{2}H_2O$: C, 54.84; H, 5.75; N, 15.99. Found: C, 54.57; H, 5.59; N, 15.53.

Example II

4-methoxy-benzoic acid (4-diethylamino-benzylidene)-hydrazide (compound 1)

To a solution of 4-methoxy-benzoic acid hydrazide (1.0 g, 0.006 mol) and 4-diethylaminobenaldehyde (1.28 g, 0.0072 mol) in abs. EtOH (20 mL) was added 3 drops of acetic acid. The reaction mixture was refluxed for 4 hours. The reaction mixture was cooled to room temperature and concentrated to remove solvent. The resulting residue was purified by flash column chromatography on silica gel ($CH_2Cl_2$/MeOH 95:5) to give yellow solid 1.49 g, in 76% yield, which was crystallized by EtOAc giving light green crystals mp: 195.5° C. 1H NMR ($CDCl_3$) δ 8.96 (brs, 1H), 8.10 (brs, 1H), 7.82 (d, 2H), 7.62 (d, 2H), 6.96 (d, 2H), 6.65 (d, 2H), 3.86 (s, 3H), 3.41 (q, 4H), 1.27 (t, 6H). 13C NMR ($CDCl_3$) δ 160.5, 159.6, 146.0, 126.7, 126.3, 126.1, 125.8, 111.2, 108.3, 108.2, 52.5, 41.5, 9.7. Anal. Calcd for $C_{19}H_{23}N_3O_2$: C, 70.13; H, 7.12; N, 12.91. Found: C, 69.86; H, 7.18; N, 12.63.

Example III

4-Methoxy-benzoic acid N'-(4-diethylamino-benzylidene)-N-(4-methyl-benzyl)-hydrazide (compound 2)

To a solution of 4-methoxy-benzoic acid (4-diethylamino-benzylidene)-hydrazide (1) (0.28 g, 0.00086 mol) in DMF (10 ml), was added α-bromo-p-xylene (0.48 g, 0.0026 mol) and powdered $K_2CO_3$ (0.83 g, 0.006 mol) and the resulting mixture heated at 45° C. overnight. After cooling to ambient temperature, the reaction mixture was diluted with water (50 mL) and extracted with EtOAc (3×30 mL). The combined organic extracts were concentrated to an oil, which was purified by flash chromatography (gradient elution, 9:1 to 7:3 Hexanes/EtOAc to give the desired product as oil 0.33 g in 88% yield. 1H NMR ($CDCl_3$) δ 7.91 (d, 2H), 7.63 (s, 1H), 7.30 (d, 2H), 7.20 (d, 2H), 7.14 (d, 2H), 6.97 (d, 2H), 6.57 (d, 2H), 5.38 (s, 2H), 3.90 (s, 3H), 3.37 (q, 4H), 2.32 (s, 3H), 1.16 (t, 6H). 13C NMR ($CDCl_3$) δ 167.3, 158.3, 145.8, 137.9, 133.8, 129.9, 126.7, 125.8, 124.2, 118.9, 111.2, 109.8, 108.3, 52.5, 42.5, 41.5, 18.2, 9.6.

Example IV

4-Hydroxy-benzoic acid (4-diethylamino-benzylidene)-hydrazide (compound 3, DY131)

$BBr_3$ (2 mL, 1.0 M solution in dichloromethane) was added dropwise to a cooled (0° C.) solution of 4-Methoxy-benzoic acid N'-(4-diethylamino-benzylidene)-N-(4-methyl-benzyl)-hydrazide (compound 2) (0.33 g, 0.00077 mol) in dried $CH_2Cl_2$ (5 mL) at −78° C. under Ar. After stirring for an additional hour at 0° C., the reaction mixture was warmed to room temperature and treated with 1:1 $CH_3OH:CH_2Cl_2$ (10 mL) with cooling and stirred 2 hr at ambient temperature. Concentration of the mixture gave oil, which was purified by flash chromatography 9:1 $CH_2Cl_2$/MeOH to give the desired product as a solid 0.13 g in 41% yield, mp: 228.4° C. 1H NMR ($CD_3OD$) δ 8.16 (s, 1H), 7.81 (d, 2H), 7.63 (d, 2H), 6.88 (d, 2H), 6.72 (d, 2H), 3.87 (d, 1H), 3.46 (q, 4H), 1.19 (t, 6H). 13C NMR ($CD_3OD$) δ 162.2, 158.2, 147.1, 146.7, 126.3, 126.2, 120.7, 117.7, 111.9, 110.6, 108.0, 41.1, 8.6. Anal. Calcd for $C_{18}H_{21}N_3O_2 \cdot \frac{1}{4} H_2O$: C, 68.43; H, 6.70; N, 13.31. Found: C, 68.36; H, 6.99; N, 13.58.

Example V

4-Hydroxy-benzoic acid hydrazide

A solution of methyl 4-hydroxybenzoate, (1.0 g, 0.0066 mol) in methanol (20 mL) was treated with hydrazine hydrate (2.65 g, 0.053 mol) and the reaction mixture heated at reflux for 48 hours. The reaction mixture was concentrated and the residue was filtered to give the desired hydrazide as solid which was washed several times with EtOAc to give a white solid 0.9 g in 90% yield, mp: 267.6° C. (ABCR GmbH&Co KG, mp: 264-266° C.). 1H NMR (DMSO-$d_6$) δ 9.46 (s, 1H), 7.67 (d, 2H), 6.77 (d, 2H), 4.34 (brs, 3H). 13C NMR (DMSO-$d_6$) δ 163.4, 157.5, 129.0, 126.3, 121.5, 112.9, 112.3. Anal. Calcd for $C_7H_8N_2O_2 \cdot \frac{1}{3}$ H2O: C, 53.16; H. 5.10; N, 17.71. Found: C, 53.48; H, 5.15; N, 17.48.

Example VI

4-Hydroxy-benzoic acid (4-diethylamino-benzylidene)-hydrazide (compound 3) (DY131)

To a solution of 4-hydroxy-benzoic acid hydrazide (0.1 g, 0.00066 mol) in abs. EtOH (10 mL) and 4-diethylaminoaldehyde (0.14 g, 0.0008 mol) was added 1 drop of acetic acid. The reaction mixture was refluxed for 4 hours. The reaction mixture was cooled to room temperature and concentrated to remove solvent. The resulting residue was purified by flash column chromatography on silica gel ($CH_2Cl_2$/MeOH 95:5) to give green solid 0.13 g, in 65% yield, mp: 232.0° C. 1H NMR ($CD_3OD$) δ 8.15 (s, 1H), 7.80 (d, 2H), 7.64 (d, 2H), 6.87 (d, 2H), 6.73 (d, 2H), 3.46 (q, 4H), 1.25 (t, 6H). 13C NMR ($CDCl_3$) δ 162.2, 158.2, 146.8, 146.7, 126.3, 120.7, 117.8, 111.9, 108.0, 41.1, 8.6. Anal. Calcd for $C_{18}H_{21}N_3O_2$: C, 69.43; H, 6.80; N, 13.49. Found: C, 69.36; H, 6.94; N, 13.36.

Example VII

4-Hydroxy-benzoic acid (3-methyl-benzylidene)-hydrazide (DY159)

To a solution of 4-hydroxy-benzoic acid hydrazide (0.2 g, 0.0013 mol) in abs. EtOH (10 mL) and m-tolualdehyde (0.32 g, 0.0026 mol) was added 1 drop of acetic acid. The reaction mixture was refluxed for 4 hours. The reaction mixture was cooling to room temperature and concentrated to remove solvent. The resulting residue was solidified by EtOAc to give white solid 0.25 g, in 76% yield, mp: 241.9° C. $^1$H NMR (CD$_3$OD) δ 8.27 (s, 1H), 7.83 (d, 2H), 7.67 (s, 1H), 7.59 (d, 1H), 7.31 (t, 1H), 7.24 (d, 1H), 6.88 (d, 2H), 2.37 (s, 3H). $^{13}$C NMR (CDCl$_3$) δ 166.9, 162.8, 150.0, 139.7, 135.7, 132.2, 130.8, 129.7, 129.1, 126.1, 124.7, 116.3, 114.9, 21.3. Anal. Calcd for $C_{15}H_{14}N_2O_2 \cdot \frac{1}{4}H_2O$: C, 69.61.; H, 5.45; N, 10.82. Found: C, 69.38; H, 5.51; N, 10.52.

Example VIII

4-Hydroxy-benzoic acid benzylidene-hydrazide (DY162)

To a solution of 4-hydroxy-benzoic acid hydrazide (0.5 g, 0.0033 mol) in abs. EtOH (10 mL) and benzaldehyde (0.35 g, 0.0033 mol) was added 1 drop of acetic acid. The reaction mixture was refluxed for 4 hours. The reaction mixture was cooling to room temperature and concentrated to remove solvent. The resulting residue was solidified by EtOAc to give white solid 0.68 g, in 86% yield, mp: 226.4° C. $^1$H NMR (CD$_3$OD) δ 8.30 (s, 1H), 7.83 (d, 4H), 7.42 (d, 3H), 6.88 (d, 2H). $^{13}$C NMR (CDCl$_3$) δ 167.5, 162.9, 149.8, 135.7, 131.4, 130.9, 129.8, 128.7, 124.9, 116.3. Anal. Calcd for $C_{14}H_{12}N_2O_2$: C, 69.99; H, 5.03; N, 11.66. Found: C, 69.82; H, 5.34; N, 11.60.

Example IX

4-Hydroxy-benzoic acid (4-methyl-benzylidene)-hydrazide (DY163)

To a solution of 4-hydroxy-benzoic acid hydrazide (0.3 g, 0.002 mol) in abs. EtOH (10 mL) and p-tolualdehyde (0.24 g, 0.002 mol) was added 1 drop of acetic acid. The reaction mixture was refluxed for 4 hours. The reaction mixture was cooling to room temperature and concentrated to remove solvent. The resulting residue was solidified by EtOAc to give white solid 0.49 g, in 96% yield, mp: 252.6° C. $^1$H NMR (CD$_3$OD) δ 8.26 (s, 1H), 7.82 (d, 2H), 7.70 (d, 2H), 7.24 (d,2H), 6.88 (d, 2H), 2.36 (s, 3H). $^{13}$C NMR (CDCl$_3$) δ 166.8, 162.7, 150.0, 142.0, 132.0, 130.5, 128.8, 124.7, 116.3, 21.5. Anal. Calcd for $C_{14}H_{12}N_2O_2$: C, 69.99; H, 5.03; N, 11.66. Found: C, 70.01; H, 5.08; N, 11.73.

Example X

4-Hydroxy-benzoic acid (2-chloro-3-trifluoromethyl-benzylidene)-hydrazide (DY165)

To a solution of 4-hydroxy-benzoic acid hydrazide (0.3 g, 0.002 mol) and 2-chloro-3-(trifluoromethyl)benzaldehyde (0.42 g, 0.002 mol) in abs. EtOH (10 mL) was added 1 drop of acetic acid. The reaction mixture was refluxed for 4 hours. The reaction mixture was cooling to room temperature and concentrated to remove solvent. The resulting residue was solidified by EtOAc to give white solid 0.64 g, in 93% yield, mp: 261.5° C. $^1$H NMR (CD$_3$OD) δ 8.89 (s, 1H), 8.51 (d, 1H), 7.85 (m, 3H), 7.56 (t, 1H), 6.89 (d, 2H). $^{13}$C NMR (CDCl$_3$) δ 166.9, 163.1, 144.3, 135.7, 132.8, 132.5, 131.0, 130.3, 130.1, 128.5, 125.4, 124.3, 123.2, 116.4. Anal. Calcd for $C_{15}H_{10}ClF_3N_2O_2 \cdot \frac{1}{2}H_2O$: C, 51.22; H, 2.86; N, 7.96; Cl, 10.08; F, 16.20. Found: C, 51.17; H, 3.04; N, 7.53; Cl, 10.25; F, 15.93.

Example XI

4-Hydroxy-benzoic acid (4-trifluoromethyl-benzylidene)-hydrazide (DY168)

To a solution of 4-hydroxybenzhydrazide (0.3 g, 0.002 mol) and 4-trifluoromethylbenzaldehyde (0.35 g, 0.002 mol) in abs. EtOH (10 mL) was added 1 drop of acetic acid. The reaction mixture was refluxed for 4 hours. The reaction mixture was cooling to room temperature and concentrated to remove solvent. The resulting residue was solidified by EtOAc to give beige solid 0.58 g, in 94% yield, mp: 260.5° C. $^1$H NMR (CD$_3$OD) δ 8.35 (s, 1H), 7.99 (d, 2H), 7.83 (d, 2H), 7.70 (d,2H), 6.87 (d, 2H). $^{13}$C NMR (CD$_3$OD) δ 167.0, 163.0, 147.7, 1139.6, 131.0, 129.1, 126.7, 126.6, 124.5, 116.4. Anal. Calcd for $C_{15}H_{11}F_3N_2O_2 \cdot \frac{1}{4}H_2O$: C, 57.60; H, 3.54; N, 8.95, F; 18.22. Found: C, 57.71; H, 3.77; N, 8.67, F; 18.43.

Example XII

4-Hydroxy-benzoic acid (4-methoxy-benzylidene)-hydrazide (DY169)

To a solution of 4-hydroxybenzhydrazide (0.3 g, 0.002 mol) and p-anisaldehyde (0.27 g, 0.002 mol) in abs. EtOH (10 mL) was added 1 drop of acetic acid. The reaction mixture was refluxed for 4 hours. The reaction mixture was cooling to room temperature and concentrated to remove solvent. The resulting residue was solidified by EtOAc to give white solid 0.51 g, in 93% yield, mp: 209.0° C. $^1$H NMR (CD$_3$OD) δ 8.23 (s, 1H), 7.82 (d, 2H), 7.76 (d, 2H), 6.97 (d,2H), 6.87 (d, 2H), 3.82 (s, 3H). $^{13}$C NMR (CD$_3$OD) δ 166.8, 163.2, 162.7, 149.8, 130.8, 130.4, 128.2, 124.8, 116.3, 115.2, 55.9. Anal. Calcd for $C_{15}H_{14}N_2O_3$: C, 66.66; H, 5.22; N, 10.36. Found: C, 66.82; H, 5.28; N, 10.38.

Example XIII

4-Hydroxy-benzoic acid (3-nitro-4-trifluoromethyl-benzylidene)-hydrazide (DY170)

To a solution of 4-hydroxy-benzoic acid hydrazide (0.3 g, 0.002 mol) and 2-nitro-4-(trifluoromethyl)-benzaldehyde (0.44 g, 0.002 mol) in abs. EtOH (10 mL) was added 1 drop of acetic acid. The reaction mixture was refluxed for 4 hours. The reaction mixture was cooling to room temperature and concentrated to remove solvent. The resulting residue was solidified by EtOAc to give white solid 0.65 g, in 92% yield, mp: 279.6° C. $^1$H NMR (DMSO-d$_6$) δ 12.20 (s, 1H), 10.19 (s, 1H), 8.84 (s, 1H), 8.39 (s, 1H), 8.31 (s, 1H), 8.16 (d, 1H), 7.83 (d, 2H), 6.86 (d, 2H). $^{13}$C NMR (DMSO-d$_6$) δ 164.9, 163.0, 150.0, 142.2, 134.6, 131.9, 131.7, 131.0, 128.1, 125.9, 125.1, 124.0, 123.8, 121.6, 117.0. Anal. Calcd for $C_{15}H_{10}F_3N_3O_4 \cdot \frac{1}{2}H_2O$: C, 49.72; H, 2.78; N, 11.60; F, 15.73. Found: C, 49.88; H, 2.76; N, 11.41; F, 15.47.

Example XIV

4-Hydroxy-benzoic acid benzo[1,3]dioxo-4-ylmethylene-hydrazide (DY174)

To a solution of 4-hydroxy-benzoic acid hydrazide (0.3 g, 0.002 mol) and 2,3(methylenedioxy)benzaldehyde (0.3 g, 0.002 mol) in abs. EtOH (10 mL), was added 1 drop of acetic acid. The reaction mixture was refluxed for 5 hours. The reaction mixture was cooling to room temperature and concentrated to remove solvent. The resulting residue was solidified by EtOAc to give red solid 0.51 g, in 89% yield, mp: 277.9° C. $^1$H NMR (DMSO-d$_6$) δ 11.66 (s, 1H), 10.11 (s, 1H), 8.53 (s, 1H), 7.80 (d, 2H), 7.25 (s, 1H), 6.95 (m, 2H), 6.84 (d, 2H), 6.11 (s, 2H). $^{13}$C NMR (DMSO-d$_6$) δ 164.6, 162.5, 149.6, 147.8, 142.4, 131.6, 125.6, 123.8, 119.6, 118.5, 116.9, 111.1, 103.4. Anal. Calcd for C$_{15}$H$_{12}$N$_2$O$_4$ · ¼H$_2$O: C, 62.38; H, 4.18; N, 9.70. Found: C, 62.27; H, 4.17; N, 9.59.

Example XV

4-Hydroxy-benzoic acid (5-methyl-thiophen-2-ylmethylene)-hydrazide (DY166)

To a solution of 4-hydroxy-benzoic acid hydrazide (0.25 g, 0.0016 mol) and 5-methyl-2-thiophenecarboxaldehyde (0.20 g, 0.0016 mol) in abs. EtOH (10 mL), was added 1 drop of acetic acid. The reaction mixture was refluxed for 4 hours. The reaction mixture was cooling to room temperature and concentrated to remove solvent. The resulting residue was solidified by EtOAc to give white solid 0.24 g, in 57% yield, mp: 215.7° C. $^1$H NMR (CD$_3$OD) δ 8.38 (s, 1H), 7.79 (d, 2H), 7.17 (s, 1H), 6.86 (d, 2H), 6.77 (s, 1H), 2.49 (s, 3H), 1.31. $^{13}$C NMR (CDCl$_3$) δ 166.5, 162.8, 145.6, 144.8, 138.1, 132.4, 130.7, 127.1, 124.8, 116.3, 15.6. Anal. Calcd for C$_{13}$H$_{12}$N$_2$O$_2$S: C, 59.98; H, 4.65; N, 10.76. Found: C, 59.98; H, 4.45; N, 10.40.

Example XVI

4-Hydroxy-benzoic acid (5-ethyl-thiophen-2-ylmethylene)-hydrazide (DY164)

To a solution of 4-hydroxy-benzoic acid hydrazide (0.3 g, 0.002 mol) and 5-ethyl-2-thiophenecarboxaldehyde (0.28 g, 0.002 mol) in abs. EtOH (10 mL), was added 1 drop of acetic acid. The reaction mixture was refluxed for 4 hours. The reaction mixture was cooling to room temperature and concentrated to remove solvent. The resulting residue was solidified by EtOAc to give white solid 0.53 g, in 96% yield, mp: 194.5° C. $^1$H NMR (CD$_3$OD) δ 8.39 (s, 1H), 7.79 (d, 2H), 7.19 (s, 1H), 6.86 (d, 2H), 6.80 (s, 1H), 2.86 (q, 2H), 1.31 (t, 3H). $^{13}$C NMR (CDCl$_3$) δ 166.5, 162.7, 153.1, 144.9, 137.7, 132.3, 130.8, 125.3, 124.8, 116.3, 24.7, 16.2. Anal. Calcd for C$_{14}$H$_{14}$N$_2$O$_2$S: C, 61.29; H, 5.14; N, 10.21. Found: C, 61.00; H, 5.18; N, 10.00.

Example XVII

4-Hydroxy-benzoic acid (5-nitro-thiophen-2-ylmethylene)-hydrazide (DY167)

To a solution of 4-hydroxy-benzoic acid hydrazide (0.3 g, 0.002 mol) and 5-nitro-2-thiophenecarboxaldehyde (0.28 g, 0.002 mol) in abs. EtOH (10 mL), was added 1 drop of acetic acid. The reaction mixture was refluxed for 4 hours. The reaction mixture was cooling to room temperature and concentrated to remove solvent. The resulting residue was solidified by EtOAc to give white solid 0.55 g, in 95% yield, mp: 194.5° C. $^1$H NMR (DMSO-d$_6$) δ 11.99 (s, 1H), 10.18 (s, 1H), 8.63 (s, 1H), 8.11 (d, 2H), 7.78 (d, 2H), 7.53 (d, 1H), 6.86 (d, 2H). $^{13}$C NMR (DMSO-d$_6$) δ 164.9, 162.9, 152.5, 149.0, 142.0, 132.4, 131.8, 131.1, 125.1, 117.0. Anal. Calcd for C$_{12}$H$_9$N$_3$O$_4$S: C, 49.48; H, 3.11; N, 14.43. Found: C, 49.55; H, 3.09; N, 14.36.

Example XVIII

4-Hydroxy-benzoic acid (4,5-dimethyl-furan-2-ylmethylene)-hydrazide (DY173)

To a solution of 4-hydroxy-benzoic acid hydrazide (0.3 g, 0.002 mol) and 4,5-dimethyl-2-furaldehyde (0.25 g, 0.002 mol) in abs. EtOH (10 mL), was added 1 drop of acetic acid. The reaction mixture was refluxed for 5 hours. The reaction mixture was cooling to room temperature and concentrated to remove solvent. The resulting residue was solidified by EtOAc to give red solid 0.47 g, in 90% yield, mp: 251.4° C. $^1$H NMR (DMSO-d$_6$) δ 11.46 (s, 1H), 10.09 (s, 1H), 8.18 (s, 1H), 7.79 (d, 2H), 6.86 (d, 2H), 6.69 (s, 1H), 2.27 (s, 3H), 1.96 (s, 3H). $^{13}$C NMR (DMSO-d$_6$) δ 163.1, 161.0, 150.3, 147.2, 137.0, 130.0, 124.4, 117.4, 116.9, 115.4, 11.8, 9.9. Anal. Calcd for C$_{14}$H$_{14}$N$_2$O$_3$ H$_2$O: C, 60.82; H, 5.11; N, 10.13. Found: C, 60.80; H, 5.03; N, 9.48.

Example XIX

4-Hydroxy-benzoic acid (5-ethyl-furan-2-ylmethylene)-hydrazide (DY175)

To a solution of 4-hydroxy-benzoic acid hydrazide (0.3 g, 0.002 mol) and 5-ethyl-2-furaldehyde (0.25 g, 0.002 mol) in abs. EtOH (10 mL), was added 1 drop of acetic acid. The reaction mixture was refluxed for 5 hours. The reaction mixture was cooling to room temperature and concentrated to remove solvent. The resulting residue was solidified by pet ether to give red solid 0.44 g, in 85% yield, mp: 60.5° C. $^1$H NMR (DMSO-d$_6$) δ 11.53 (s, 1H), 10.16 (s, 1H), 8.24 (s, 1H), 7.79 (d, 2H), 6.87 (d, 2H), 6.81 (s, 1H), 2.71 (q, 2H), 1.24 (t, 3H). $^{13}$C NMR (DMSO-d$_6$) δ 164.5, 162.1, 161.2, 149.8, 138.5, 131.5, 125.7, 116.9, 116.7, 108.9, 22.8, 13.8. Anal. Calcd for C$_{14}$H$_{14}$N$_2$O$_3$: C, 65.11; H, 5.46; N, 10.85. Found: C, 65.00; H, 5.36; N, 10.55.

Example XX

4-Hydroxy-benzoic acid (3,5-dimethyl-1H-pyrrol-2-ylmethylene)-hydrazide (DY171)

To a solution of 4-hydroxy-benzoic acid hydrazide (0.3 g, 0.002 mol) and 3,5-dimethyl-pyrrole-2-carboxaldehyde (0.25 g, 0.002 mol) in abs. EtOH (10 mL), was added 1 drop of acetic acid. The reaction mixture was refluxed for 5 hours. The reaction mixture was cooling to room temperature and concentrated to remove solvent. The resulting residue was solidified by EtOAc to give grey solid 0.44 g, in 86% yield, mp: 261.2° C. $^1$H NMR (CD$_3$OD) δ 8.12 (s, 1H), 7.79 (d, 2H), 6.88 (d, 2H), 5723 (s, 1H), 2.24 (s, 3H), 2.13 (s, 3H). $^{13}$C NMR (CD$_3$OD) δ 166.5, 162.5, 139.4, 134.1, 130.5, 127.1, 124.9, 124.1, 116.3, 110.7, 12.9, 10.7. Anal. Calcd for $C_{14}H_{15}N_3O_2$: C, 65.35; H, 5.88; N, 16.33. Found: C, 65.52; H, 5.79; N, 16.30.

Example XXI

4-Hydroxy-benzoic acid (4-bromo-3,5-dimethyl-1H-pyrrol-2-ylmethylene)-hydrazide (DY172)

To a solution of 4-hydroxy-benzoic acid hydrazide (0.06 g, 0.0004 mol) and 4-bromo-3,5-dimethyl-pyrrole-2-carboxaldehyde (0.08 g, 0.0004 mol) in abs. EtOH (5 mL), was added 1 drop of acetic acid. The reaction mixture was refluxed for 5 hours. The reaction mixture was cooling to room temperature and concentrated to remove solvent. The resulting residue was solidified by EtOAc to give red solid 0.1 g, in 77% yield, mp: 235.4° C. $^1$H NMR (DMSO-$d_6$) δ 11.46 (s, 1H), 11.21 (s, 1H), 9.99 (s, 1H), 8.26 (s, 1H), 7.76 (d, 2H), 6.82 (d, 2H), 2.15 (s, 3H), 2.03 (s, 3H). $^{13}$C NMR (DMSO-$d_6$) δ 163.9, 162.2, 140.2, 131.6, 131.3, 126.1, 124.0, 124.3, 116.8, 13.4, 11.8. Anal. Calcd for $C_{14}H_{14}BrN_3O_2 \cdot \frac{1}{4}H_2O$: C, 49.35; H, 4.14; N, 12.33; Br, 23.69. Found: C, 49.21; H, 3.95; N, 11.96; Br, 23.37.

Example XXII

4-[N'-(3,5-Bis-trifluoromethyl-benzylidene)-hydrazino]-6-chloro-[1,3,5]triazin-2-ol (DY176)

To a solution of 4-chloro-6-hydrazino-[1,3,5]triazin-2-ol (0.13 g, 0.0008 mol) and 3,5-bis(trifluoromethyl)benz aldehyde (0.39 g, 0.0016 mol) in abs. EtOH (10 mL), was added 1 drop of acetic acid. The reaction mixture was refluxed for 5 hours. The reaction mixture was cooling to room temperature and concentrated to remove solvent. The resulting residue was solidified by EtOAc to give red solid 0.21 g, in 72% yield, mp: 258.3° C. $^1$H NMR (DMSO-$d_6$) δ 11.15 (s, 1H), 8.97 (s, 1H), 8.54 (s, 1H), 7.59 (s, 1H), 7.30 (s, 2H). $^{13}$C NMR (DMSO-$d_6$) δ 179.0, 160.2, 149.8, 148.8, 128.3, 127.6, 125.4, 124.7.

Example XXIII

Transfection Assays

To test the effect of the compounds on ERR and ER, CV-1 cells were transiently transfected with expression vectors for the receptors along with appropriate reporter constructs according to methods known in the art. The receptors to be tested were expressed in CV-1 cells. Suitable reporter gene constructs are well known to skilled workers in the fields of biochemistry and molecular biology. All transfections additionally contained an expression vector with a cytomegalovirus promoter (pCMV-β-gal) as an internal control. Suitable constructs for use in these studies may conveniently be cloned into a cytomegalovirus expression vector (pCMV). For example, pCMV-β-gal contains the *E. coli* β-galactosidase gene expressed under control of the cytomegalovirus promoter/enhancer. Other vectors known in the art can be used in the methods of the present invention.

Genes encoding the following previously described proteins, which are suitable for use in the studies described herein, were cloned into a cytomegalovirus expression vector. All accession numbers in this application refer to GenBank accession numbers. GAL4 fusions containing receptor ligand binding domain fragments were constructed by fusing human ERRalpha, human ERRbeta and murine ERRgamma ligand binding domain sequences to the C-terminal end of the yeast GAL4 DNA binding domain (amino acids 1-147 accession X85976) to form the expression vectors GAL-hERRa, GAL-L-hERRb and Gal-mERRg, respectively. HRHN-GAL is a control containing the yeast GAL4 DNA binding domain without receptor sequences. CMV-PGC-1a contains and expressed the PGC-1a coding sequences derived from PGC-1a (accession NM__008904). CMV-β-gal, used as a control gene for comparison with the activation of the receptor or receptor domain being tested, contains the *E. coli* β-galactosidase coding sequences derived from pCH110 (accession U02445). This gene was conveniently used here, however, any unrelated gene which is available and for which a convenient assay exists to measure its activation may be used as a control with the methods of this invention.

CV-1 cells for the activation assays were grown in Dulbecco's modified Eagle's medium supplemented with 10% resin charcoal-stripped fetal bovine serum, 50 U/ml penicillin G and 50 μg/ml streptomycin sulfate (DMEM-FBS) at 37° C. in 5% $CO_2$. One day prior to transfection, cells were plated to 50-80% confluence using phenol red free DMEM-FBS.

The cells were transiently transfected by lipofection but other methods of transfection of DNA into cells can be utilized without deviating from the spirit of the invention. Luciferase reporter construct UASgx4-TK-Luc (300 ng/$10^5$ cells) and cytomegalovirus-driven expression vector HRHN-GAL, GAL-hERRa, GAL-L-hERRb or Gal-mERRg were added (5-50 ng/$10^5$ cells), with CMV-β-gal (500 ng/$10^5$ cells) as an internal control. Where indicated, CMV-PGC-1a was also added (25 ng/$10^5$ cells). After 2 hours, the liposomes were removed and the cells were treated for approximately 42 hours with phenol red free DMEM-FBS containing the test compounds.

Papers and patents listed in the disclosure are expressly incorporated by reference in their entirety. It is to be understood that the description, specific examples, and figures, while indicating preferred embodiments, are given by way of illustration and exemplification and are not intended to limit the scope of the present invention. Various changes and modifications within the present invention will become apparent to the skilled artisan from the disclosure contained herein and may be made without departing from the spirit of the present invention. Therefore, the spirit and scope of the appended claims should not be limited to the description of the preferred versions contained herein.

The invention claimed is:

1. A compound selected from the group consisting of,

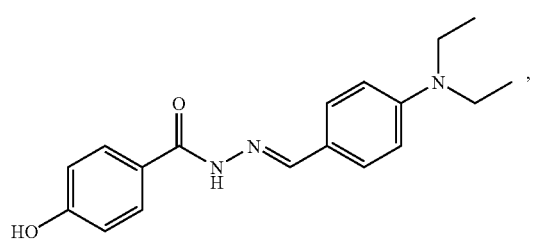

-continued
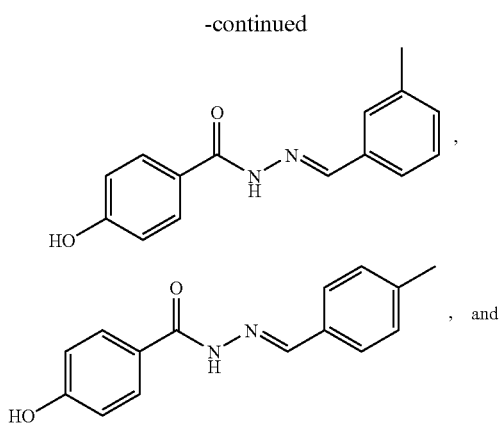
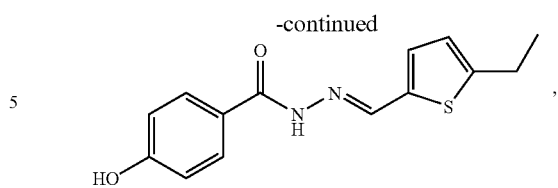
wherein said compound is an Estrogen-Related Receptor (ERR) agonist.
2. The compound of claim 1, wherein the compound is an ERRα/β/γ specific agonist.
3. The compound of claim 1, wherein the compound is an ERRβ/γ specific agonist.
4. The compound of claim 1, wherein the compound is an ERRγ specific agonist.
* * * * *